United States Patent [19]

Witiak et al.

[11] Patent Number: 5,130,426

[45] Date of Patent: Jul. 14, 1992

[54] SYNTHESIS OF BIS (MORPHOLINOMETHYL) DERIVATIVES OF TRICYCLIC BIS (DIOXOPIPERAZINES)

[75] Inventors: Donald T. Witiak, Vernon, Ohio; Bharat K. Trivedi, Canton, Mich.

[73] Assignee: Ohio State University, Columbus, Ohio

[21] Appl. No.: 749,514

[22] Filed: Jun. 27, 1985

[51] Int. Cl.$^5$ .................................... C07D 413/00
[52] U.S. Cl. ........................................ 544/115
[58] Field of Search ................................ 544/115

[56] References Cited

FOREIGN PATENT DOCUMENTS 0125475 11/1984 European Pat. Off. .
60-25975 8/1985 Japan .

OTHER PUBLICATIONS

Herman et al, 19 Adv. Pharmacol. and Chemother., 249 (1982).
Witiak et al, 21 J. Med. Chem., 1194 (1978).
Witiak et al., 24 J. Med. Chem., 1329 (1981).
Ren et al., Kexue Tongbao, 1980:25, 189.
Ren, abstract of Japanese patent Application No. 58-132657, published in Central Patents Index-Derwent Publications, London, England, 1985, Week 8512, p. 10 on about May 1, 1985.
Ren abstract, At—2153(MST-02) presented at the 14th International Congress of Chemotherapy, Kyoto, Japan, 1985.

*Primary Examiner*—C. Warren Ivy
*Assistant Examiner*—Raymond Covington

[57] ABSTRACT

Bis(morpholinomethyl) derivatives of tricyclic bisdioxopyperzaines of the formula

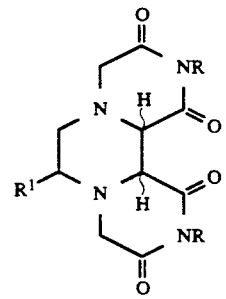

wherein R is H,

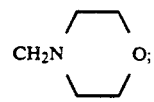

R' is H, lower alkyl groups (straight or branched chain of 1 to 6 carbon atoms) and the processes for the syntheses thereof are provided.

6 Claims, No Drawings

SYNTHESIS OF BIS (MORPHOLINOMETHYL) DERIVATIVES OF TRICYCLIC BIS (DIOXOPIPERAZINES)

BACKGROUND OF THE INVENTION

Bis(dioxopieperazines) are of considerable import owing to their antimetastatic properties and their actions ameliorating anthracycline-induced toxicity in animals as reported by Herman et al., 19 Adv. in Pharmacol. and Chemother. 249(1982). Cyclopropyl-bis(dioxopiperazines), as reported in Witiak et al., 21 J. Med. Chem., 1194(1978) and Zwilling et al, 44 Brit. J. Cancer 578 (1981), and related tetraazaperhydrophenanthrenes as reported in Witiak et al, 24 J. Med. Chem. 1329 (1981) have been employed to assess stereoselective antimetastatic properties. Although a "cisoid" relationship of dioxopiperazine rings seems to be important for antimetastatic activity, pretreatment of B16F10 cells for 24 hours with trans-anti-trans-1, but not cis-syn-trans-2, significantly inhibited metastases following their injection into the tail vein of C57B1/6J mice, as reported by Witiak et al., 24 J. Med. Chem., 1329 (1981).

A morpholinomethyl analogue of ICRF-154, an open chain compound related to compounds 1 and 2 shown below, namely bis-(4-morpholinomethyl-3,5-dioxopiperazinyl-1,2-ethane) was reported by Ren et al. Kexue Tongbao, 1980:25, 189, to be active, by both the oral and ip routes, against various experimental tumors. Results of the clinical investigations in China indicated that this compound may be useful in the treatment of malignant lymphomas, uveitis, sympathetic ophthalmitis and psoriasis (Ren et al., supra). It is therefore apparent that the correlation between the structure of morpholinomethyl-N groups and their behavior in vivo is not well-understood and there is a continuing need for the development of pharmacologically and clinically effective antitumor, anti-metastatic bis(morpholinomethyl) derivatives of tricyclic bis(dioxopiperazines).

SUMMARY OF THE INVENTION

The present invention relates to novel bis(morpholinomethyl) derivatives of tricyclic bis(dioxopiperazines), which are compounds of the formula:

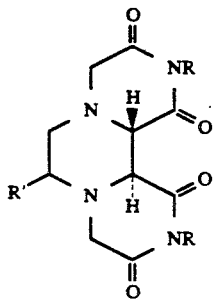

I

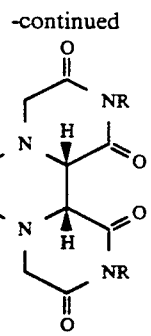

II wherein R=H,

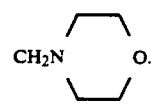

R'=H, or alkyl [straight or branched chain of 1 to 6 carbons], their distereomers or mixtures thereof or a pharmaceutically acceptable acid addition salt thereof.

The present invention also relates to a pharmaceutical composition comprising a therapeutically effective amount of a compound of the above formula I or II with a pharmaceutically acceptable carrier and to a method of treating mammals by administering to such mammals a dosage form of a compound of the formula I or II as defined above.

The present invention further relates to a process for the synthesis of the bis(morpholinomethyl) derivatives of tricyclic bis(dioxopiperazines).

DESCRIPTION OF THE INVENTION

A. Chemistry

Morpholinomethyl-N groups impart antineoplastic properties to a molecule owning to possible alkylating activities not unlike those proposed by Soloway et al., 102 J. Theor. Biol, 361 (1983), for certain hydroxymethyl-N metabolites of therapeutically useful drugs.

The morpholinomethyl derivatives 3 and 4 of the present invention were prepared to investigate their stereoselectivity in the Lewis Lung carcinoma (LL) model.

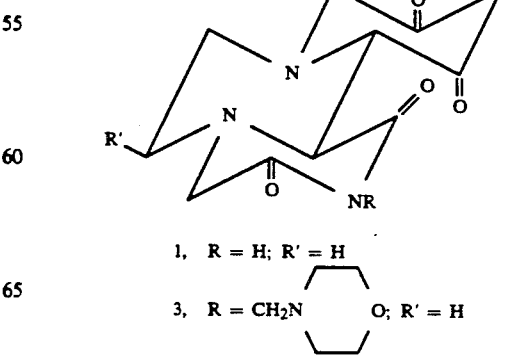

1, R = H; R' = H

3, R = CH₂N◯O; R' = H

-continued

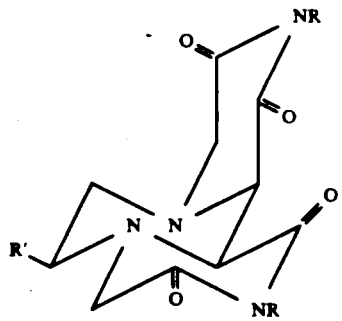

2, R = H; R' = H

4, R = CH$_2$N⌒O; R' = H

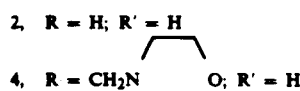

Tricyclic analogues trans-anti-trans-1 and cys-syn-trans-2 having a "cisoid" relationship of dioxopiperazine rings were constructed.

Starting saturated diamide 7 was prepared from pyrazine-2,3-dicarboxamide 5 according to the method of Felder et al., *Helv. Chim. Acta.* 33, 888 (1960).

Reaction of diamide 7 with either methyl or ethyl bromacetate in Me$_2$SO at room temperature afforded diester diamide 10 and 11, respectively, in 88 and 91% yield. Diester diamide 10 was quantitatively converted to 12 during chromatography on silica gel using MeOH as the eluant. Alkylation of 7 with methyl bromoacetate in Me$_2$SO at 65° C. for 6 hours did not afford 10 but instead generated a mixture of bicyclic 12 and cis tricyclic 2 analogues in 51 and 14% yield, respectively.

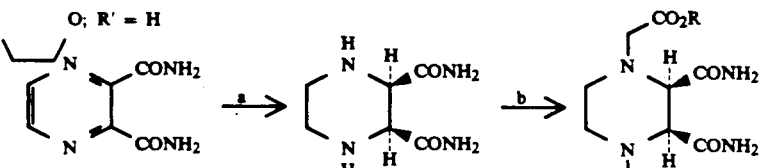

(5)   (7)   (10) R = CH$_3$
              (11) R = C$_2$H$_5$

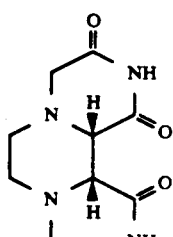 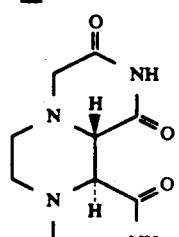 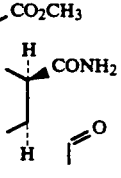

(2)   (1)   (12)

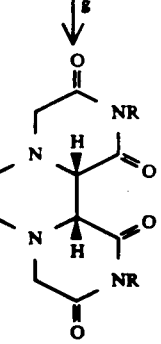 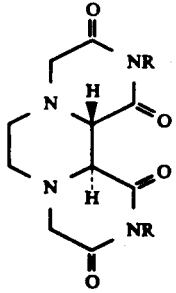

(4)   (3)

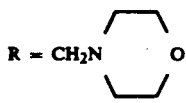

R = CH$_2$N⌒O a=EtOH, 10% Pd/C, 50 psi; b=BrCH$_2$CO$_2$Me for 10, BrCH$_2$CO$_2$Et for 11, Me$_2$SO, room temperature; c=BrCH$_2$CO$_2$Me; Me$_2$SO; 65° C., 6h; d=silica gel- MeOH; e=NaOMe/MeOH; f=NaOEt/EtOH; g=DMSO,

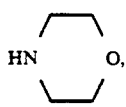

HCHO, 55° C., 5h; h=DMSO,

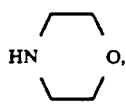

HCHO, 55° C., 5h.

Treatment of either 10, 11, or 12 with NaOMe/MeOH afforded only the trans isomer 1 in 67, 71 or 70% yield, respectively. No cis isomer was detected in the reaction mixture. However, when 10 or 11 was treated with NaOEt/EtOH under identical reaction conditions, the cis tricyclic isomer 2 was formed exclusively kn 65 and 70% yield, respectively. Neither ester 10 or 11 could be converted to tricyclic compounds 1 or 2 in the absence of base. Exclusive formation of trans-1 in NaOMe/MeOH was attributed to the complete solubility of reactants and products. Epimerization of cis-2 to the thermodynamically more stable trans-1 isomer in NaOMe/MeOH was not quantitative. Only a 60% yield of a cis/trans isomeric mixture was obtained in a ratio of approximately 1:3 (NMR analysis). Thus, epimerization of starting materials or intermediates mainly accounts for the exclusive formation of trans-1 from 10 or 11 in NaOMe/MeOH. Possibly, biphasic base-catalyzed conversion of 10 or 11 to cis-2 occurred without epimerization owing to insolubility of either reactants or products in NaOEt/EtOH.

In addition to conformational analysis of reaction sequences, stereochemical assignments were based in part on $^1$H NMR spectral analysis. In 7, and 10 the methine proton resonance signals appeared as sharp singlets at $\delta$3.38, and 3.54, respectively, owing to their chemical equivalency. For 12 one methine proton resonance signal appeared at $\delta$3.95 (CHCONHCO). The methine proton $\alpha$ to the amide function in 12 has a resonance signal at $\delta$3.39 and in this regard is close to the analogous chemical shift for 7 and 10 in $D_2O$. However, in the case of 12, the methine protons are chemically nonequivalent and cis coupling of $J=3.8$ Hz was observed.

Inspection of Dreiding molecule models revealed the chiral trans-anti-trans isomer 1 to have a twofold axis of symmetry, whereas individual conformers of the cis-syn-trans isomer 2 are asymmetric, as reported by K. Mislow "Introduction to Seereochemistry", W. A. Benjamin, N.Y., 1965, pp 97–100. However, the latter, on a rapid interconversion time scale, has an effective plane of symmetry rendering an achiral (meso) compound. For 2, as the temperature is increased from 25° to 80° C. the $^1$H NMR spectrum in $Me_2SO\text{-}d_6$ simplifies. At room temperature a simpler $^1$H NMR spectrum was observed for 1 were compared to 2. In contrast to 2, the $^1$H NMR spectrum for 1 exhibited no change at the higher temperature in $Me_2SO\text{-}d_6$. In 1, sharp methylene ($\delta$2.49, H) and methine ($\delta$4.04, 2 H) proton resonance signals were observed for the central piperazine ring. Likewise, the methylene proton resonance signals of the dioxopiperazine rings showed a sharp AB quartet ($\delta_A$ 3.48, $\delta_B$3.41 with $J_{AB} =16$ Hz). On the other hand, cis-2 showed a broad singlet at $\delta$5.2 for the methine protons, and all methylene proton resonance signals were complex multiplets. Analogues 1 and 2 exhibited virtually identical fragmentation patterns in their mass spectra with m/e 252 ($M^+$).

B. Biological Evaluation

Fifty $BDF_1$ female mice (19–21 g) were sorted at random into 5 groups of 10 mice and treatment was summarized in Table I. LL [Lewis Lung Carcinoma]($10^5$ cells in 0.05 ml) was implanted in the right hind leg on day 0. At day 10 the tumor-bearing legs were amputated. Mice showed no weight loss due to drug toxicity in any of the treatment groups. Dying mice were autopsied. No mouse had regrowth of primary tumor at the amputation site and all developed extensive metastasis in the lungs, the only organ in which they were found. Mice surviving at 50 days following implantation were killed and autopsied. All but two appeared free of tumor and these are noted in the footnote in Table I.

When treated by the above procedure, the compounds 1, 2, 3 and 4 produced the following changes in ILS. Using either the pre- or postamputation schedules, both morpholinomethyl analogues inhibited metastases, but cis-syn-trans-4 was the more effective stereoisomer. Furthermore, 4 significantly increased life span when employed using the postamputation schedule. The reverse stereoselective activity was observed for 1 and 2 when B16-F10 melanoma cells were pretreated in vitro, as disclosed by Witiak et al., 24 J. Med. Chem. 1329 (1981). The cis-syn-trans-4 analogue is not primarily exerting its action following metabolic transformation to 2, but rather exhibits intrinsic antineoplastic properties, reflecting macromolecular alkylation by a compound possessing an appropriate geometry different than that required for the parent antimetastatic bis(dioxopiperazines).

The morpholinomethyl geometric isomers (3–4) were compared with the parent compounds (1–2) using the post amputation schedule. Results are summarized in Table II. Again, cis morpholinomethyl analogue 4 was the most effective inhibitor of metastasis and provided the greatest number of 50 day survivors. The trans morpholinomethyl analogue 3 also exhibited significant activity, which was clearly better than that observed for parent trans 1. The parent cis 2 provided for a significant increase in life span of treated mice. Thus, the stereoselective effect in the LL model was reversed from that observed in the B16-F10 study reported by Witiak et al., 24 J. Med. Chem., 1329 (1981). These results differ from the structure-activity interpretations based on X-ray diffraction analyses of 1 and 2 as reported in Hempel et al., 105 J. Med. Chem. Soc., 2350 (1983). Increased activity observed for the morpholinomethyl derivatives either reflects differences in solubility and delivery (pro-drug) or an intrinsic antitumor activity of the morpholinomethyl-N functionality.

The following experiments further support the invention.

EXAMPLE 1

Dimethyl cis-2,3-Dicarbamoyl-1,4-piperazinediacetate 10. Methyl bromoacetate (2.93 g, 1.6 mL, 19.18 mmol) was slowly added (10 min; using a syringe) to a suspension of 7 (1.5 g, 8.72 mmol) and anhydrous $K_2CO_3$ (1.32 g. 9.59 mmol) in 10 mL of $Me_2SO$ under argon at room temperature. The reaction mixture was stirred at room temperature for 3 hours and diluted with 150 mL of EtOAc. The inorganic salt was filtered, and the solvent was removed under reduced pressure. $Me_2SO$ was removed at 0.3 mm (50° C.). The residue was dissolved in a minimum amount of absolute and diluted with 100 mL of EtOAc-hexane (1:1). The oil was solidified upon heating on a steam bath, filtered, and dried, affording 2.72 g of white solid. Recrystallization from MeOH-hexane yielded 2.42 g (88%) of a colorless compound 10; mp 172°–173° C.; Anal. ($C_{12}H_{20}N_4O_6$)C, H, N.

EXAMPLE 2 trans-Tetrahydrodipyrazino[1,2-a:2',1'-c] pyrazine-1, 3, 10, 12 (2H, 4H, 9H, 11H)-tetrone 1. Method A. To a suspension of diester diamide 10 (1.0 g, 3.16 mmol) in 6 mL of absolute MeOH was slowly added (~10 min) 1.8 mL of NaOMe (25% solution in absolute MeOH, 7.9 mmol) under argon at room temperature. The resulting colorless solution was heated at 60° C. for 4 hours and stirred at room temperature for 16 hours. The solvent was removed under reduced pressure, and the residual white solid was dissolved in 3 mL of $H_2O$. The aqueous solution was acidified (concentrated HCl, pH ~2), and the colorless solid was filtered, washed with 5 mL of cold $H_2O$ followed by 5 mL EtOH, and dried; yield 0.54 g, (67%); mp 284°–285° C. dec; Anal. ($C_{10}H_{12}N_4O_4$) C, H, N.

Method B. A homogeneous solution of the diester diamide 11 (0.3 g, 0.872 mmol) in 3 mL of absolute MeOH containing 0.080 g of Na was heated at 85° C. for 6 hours and at room temperature for 14 hours. Following workup as previously described, 0.159 g (71%) of crystalline compound was obtained, which was identical in all respects with trans tricyclic compound 1 prepared from diester diamide 10.

EXAMPLE 3 cis-Tetrahydrodipyrazino[1,2-a:2',1'c]pyrazine-1, 3, 10, 12, (2H, 4H, 9H, 11H)-tetrone 2. Methyl bromoacetate (2.22 g, 14.5 mmol) was slowly added to a suspension of diamide 7 (1.0 g, 5.8 mmol) and anhydrous $K_2CO_3$ (1.8 g, 13 mmol) in 6 mL of $Me_2SO$ under argon at room temperature. The reaction was heated at 65° C. for 6 hours, cooled to room temperature, and diluted with 70 mL of EtOAc. The inorganic salt was filtered, and the solvent was evaporated under reduced pressure. $Me_2SO$ was removed at 0.3 mm (50° C.). The residue was dissolved in a minimum amount of absolute MeOH and diluted with 50 mL of EtOAc-hexane (1:1). The resulting solid was stirred in 30 mL of hot MeOH (steam bath), filtered, and dried; yield 0.21 g (14%); mp 282°–284° C. dec; Anal. ($C_{10}H_{12}N_4O_4$) C, H, N.

EXAMPLE 4

Methyl trans-1-(aminocarbonyl)octahydro-7,9-dioxo-2H-pyrazino[1,2-a] pyrazine-2-acetate 12. The filtrate resulting from the isolation of 2 upon concentration under reduced pressure and recrystallization from MeOH-hexane, afforded 0.84 g (51%) of 12; mp 214°–216° C. dec; IR Anal. ($C_{11}H_{16}N_4O_5$) C, H, N.

EXAMPLE 5

Diethy cis-2,3-Dicarbamoyl-1,4-piperazinediacetate 11. To a suspension of 7 (1.0 g, 5.81 mmol) and anhydrous $K_2CO_3$ (1.8 g, 13 mmol) in 5 mL of $Me_2SO$ was added ethyl bromoacetate (2.42 g, 14.5 mmol) under argon at room temperature. The reaction mixture was stirred at room temperature for 20 hours and diluted with 50 mL of EtOAc. The mixture was filtered and the filtrate was concentrated under reduced pressure. $Me_2SO$ was removed at 0.3 mm (50° C.). The residue was dissolved in 20 mL of MeOH-EtOAc (1:1) and diluted with 100 mL of hexane. As the solution was standing at room temperature, 1.81 g (91%) of 11 crystallized: mp 120°–121° C.; Anal. ($C_{14}H_{24}N_4O_6$)C, H, N.

EXAMPLE 6 cis-Tetrahydrodipyrazino[1,2-a:2',1'-c]pyrazine-1, 3, 10, 12(2H, 4H, 9H, 11H)-tetrone 2. Method A. The diester diamide 11 (0.65 g, 1.88 mmol) was added to a solution of Na (0.173 g) in 7 mL of absolute EtOH at room temperature under argon. The resulting suspension in NaOEt was heated at 85° C. for 6 hours, during which time the reaction mixture became turbid. Following stirring at room temperature for 14 hours, the solvent was removed under reduced pressure, and the residual solid was dissolved in 3 mL of $H_2O$. The aqueous solution was acidified (concentrated HCl, pH 2), and the crystalline compound obtained upon cooling in the refrigerator was filtered, washed with 5 mL of cold $H_2O$ followed by 5 mL of ethanol, and dried: yield 0.333 g (70%); mp 282°–284° C. dec. This compound was identical in all respects with the cis tricyclic compound 2 prepared from diamide 7 as previously described.

Method B. A suspension of the diester diamide 10 (0.300 g, 0.949 mmol) in 3 mL of absolute EtOH containing 0.087 g of Na was stirred at 85° C. for 6 hours and at room temperature for 14 hours. Following workup as described above, 0.156 g (65%) of crystalline 6 was obtained.

EXAMPLE 7

2,11-Bis(morpholinomethyl)-cis-tetrahydrodipyrazino [1,2-a:2',1'-c]pyrazine-1, 3, 10, 12(2H, 4H, 9H, 11H)-tetrone 3. To a suspension of trans-anti-trans-1 (2.5 g; $9.9 \times 10^{-3}$ mol) in 25 ml of DMSO was added 3 ml of morpholine and 3 ml of 37% HCHO. The mixture was heated at 55° C. for 5 hours and the DMSO removed under reduced pressure. The residue was triturated with 20 ml of cold EtOH and the white solid filtered, washed with 20 ml of EtOH and dried affording 3.29 g (71.7%) of crystals mp 216°–218° C. Anal. calcd. for $C_{20}H_{30}N_6O_6$. C, 53.32; H, 6.71; N, 18.66. Found C, 53.19; H, 6.80; N, 18.58.

EXAMPLE 8

2,11-Bis(morpholinomethyl)-cis-tetrahydrodipyrazino [1,2-a:2',1'-c]pyrazine-1, 3, 10, 12(2H, 4H, 9H, 11H)-tetrone r. This was prepared from cis-syn-trans-2 according to the preparation of 3 from 1 affording 3.4 g (76%) of white crystals mp 212°–214° C. Anal. calcd for $C_{20}H_{30}N_6O_6$. C, 53.32; H, 6.71; N, 18.66. Found C, 53.14; H, 6.84; N, 18.51.

From the foregoing description, one skilled in the art can easily ascertain the essential characteristics of this invention and, without departing from the spirit and scope thereof, can make various changes and modifications of the invention to adapt it to various usages and conditions.

TABLE I

Lewis Lung Carcinoma (LL) Metastasis Study[a]

| | SURVIVAL DATA | | | | AUTOPSY DATA[b] | | | | | |
|---|---|---|---|---|---|---|---|---|---|---|
| | | | | | % mice | Av. number | Av. Number (and %) metast. in each size range | | | Av. Lung |
| | Survival days | MST[c] | % ILS[d] | N/T[e] | with no metast. | metast./ mouse | <1 mm | 1-2 mm | >2 mm | wt./mouse (mg) |
| 1. Control | 30, 30, 31, 32, 33, 34, 37, 37, 41, 44 | 33.5 | | 0/10 | 0% | 17.5 | 0.2 (1) | 5.4 (31) | 11.9 (68) | 942 |
| Preamput. Schedule[f] | | | | | | | | | | |
| 2. Trans-3 | 30, 31, 37, 38, 38, 39, 41, >50, >50, >50 | 38.5 | 15 | 3/10 | 30% | 15.0 | 0.2 (1) | 5 (33) | 9.8 (66) | 754 |
| 3. Cis-4 | 30, 32, 33, 36, 37, 41, >50, >50, >50, >50 | 39 | 16 | 4/10 | 40% | 12.8 | 1.0 (8) | 3.5 (27) | 8.3 (65) | 641 |
| Postamput. Schedule[g] | | | | | | | | | | |
| 4. Trans-3 | 30, 32, 33, 33, 35, 35, 40, 43, >50, >50 | 35 | 4 | 2/10 | 20% | 13.8 | 0.6 (4) | 3.8 (28) | 9.4 (68) | 752 |
| 5. Cis-4 | 30, 34, 40, 43, >50, >50, >50, >50, >50, >50 | >50 | >49 | 6/10[h] | 40% | 7.7 | 0.3 (4) | 2.6 (34) | 4.8 (62) | 538 |

[a]For these studies 10 BDF$_1$ +$^\circ$/group weighing 19-21 g were employed. Implantation was on day 0. Amputation was on day 10.
[b]Survivors killed and autopsied on day 50. Data is the average of 10 mice (dying and killed mice included).
[c]Median survival time (days).
[d]Percent ILS of 25 indicates activity.
[e]Number of 50-day survivors/total mice.
[f]Preamputation schedule = 160 mg/kg ip from −1 hr day 0 qd2x5. Solutions were prepared daily in 0.9% NaCl solutions.
[g]Postamputation schedule = 160 mg/kg ip from day 11 q2dx4. Solutions were prepared daily in 0.9% NaCl solutions.
[h]2/6 mice killed had each one metastasis (5 mm diameter).

TABLE II

Comparison of Analogues 1–4 in the Lewis Lung Carcinoma (LL) Metastasis Study using the Post Amputation Schedule[a]

| | SURVIVAL DATA | | | | AUTOPSY DATA[b] | | | | |
|---|---|---|---|---|---|---|---|---|---|
| | | | | | | | Av. No. of Metastasis | | |
| Compd. | Survival days | MST[c] | % ILS[d] | N/T[e] | Av. Body Wt. (g) | Av. Lung Wt. (mg) | <2 mm | <2 mm | M/T[f] |
| Control | 28, 32, 32, 33, 34, 34, 39, >50 | 33.5 | | 1/8 | 17.6 | 765 | 0 | 14 | 7/8 |
| 1 | 30, 31, 33, 34, 39, 39, 41, >50, >50 | 39.0 | 16 | 2/9 | 17.7 | 749 | 2 | 13 | 7/9 |
| 2 | 29, 33, 34, 41, 49, >50, >50, >50 | 45.0 | 34 | 3/8 | 17.8 | 813 | 1 | 14 | 5/8 |
| 3 | 26, 32, 34, 39, >50, >50, >50, >50, >50 | >50 | >49 | 5/9 | 19.4 | 564 | 0 | 9 | 4/9 |
| 4 | 34, 34, >50, >50, >50, >50, >50, >50, >50 | >50 | >49 | 7/9 | 19.9 | 369 | 0 | 3 | 1/9 |

[a]BDF$_1$ female (19–21 g) mice; implantation on day 0; amputation on day 9. Post amputational schedule: 160 mg/kg from day 9, q2dx4 (ip). Drugs 1 and 2 were administered in suspension (0.9% NaCl solution), whereas drugs 3–4 were soluble in saline solution.
[b]Autopsy data of dying mice and mice killed day 50.
[c]Median survival time (days).
[d]Increase in life span of 25% or greater indicates activity.
[e]Number of 50 day survivors/total mice.
[f]Number of mice with metastasis/total.

We claim:

1. A compound of the formula:

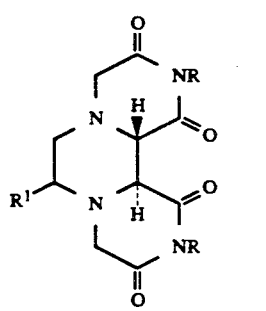

wherein R is

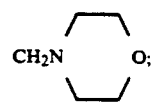

R' is H, lower alkyl group (straight or branched chain of 1–6 carbon atoms).

2. A compound of the formula:

wherein R is

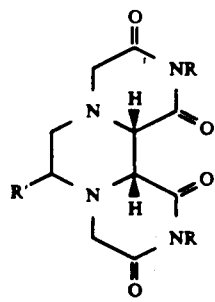

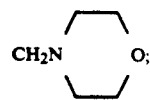

R' is H,, lower alkyl group (straight or branched chain of 1 to 6 carbon atoms).

3. A compound as claimed in claim 1, wherein R' is hydrogen or methyl.

4. A compound as claimed in claim 3, and being 2,11-bis(morpholinomethyl)-trans-tetrahydrodipyrazino [1,2-a:2',1'-c]-pyrazine-1, 3,10,12(2$\underline{H}$, 4$\underline{H}$, 9$\underline{H}$, 11$\underline{H}$)-tetrone.

5. A compound as claimed in claim 2, wherein R' is hydrogen or methyl.

6. A compound as claimed in claim 5 and being 2, 11-bis(morpholinomethyl)-cis-tetrahydrodipyrazino [1, 2-A:2',1'-c] pyrazine-1,3,10,12(2$\underline{H}$, 4$\underline{H}$, 9$\underline{H}$, 11$\underline{H}$)-tetrone.

* * * * *